(12) United States Patent
Rush

(10) Patent No.: US 8,467,972 B2
(45) Date of Patent: Jun. 18, 2013

(54) CLOSED LOOP BLOOD GLUCOSE CONTROL ALGORITHM ANALYSIS

(75) Inventor: Benjamin Rush, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 76 days.

(21) Appl. No.: 12/769,634

(22) Filed: Apr. 28, 2010

(65) Prior Publication Data

US 2010/0274497 A1  Oct. 28, 2010

Related U.S. Application Data

(60) Provisional application No. 61/173,598, filed on Apr. 28, 2009.

(51) Int. Cl.
- G01N 33/48 (2006.01)
- G01N 31/00 (2006.01)
- G06G 7/48 (2006.01)
- G06G 7/58 (2006.01)

(52) U.S. Cl.
USPC ............ 702/19; 702/22; 703/11; 703/12

(58) Field of Classification Search
None
See application file for complete search history.

(56) References Cited

U.S. PATENT DOCUMENTS

| | | |
|---|---|---|
| 2,915,579 A | 12/1959 | Mendelsohn |
| 3,374,337 A | 3/1968 | Burley |
| 3,510,747 A | 5/1970 | Petrides |
| 3,606,592 A | 9/1971 | Madurski et al. |
| 3,750,687 A | 8/1973 | Williams |
| 3,843,455 A | 10/1974 | Bier |
| 3,923,060 A | 12/1975 | Elinwood |
| 3,930,493 A | 1/1976 | Williamson |
| 3,938,140 A | 2/1976 | Garcia et al. |
| 3,994,799 A | 11/1976 | Yao et al. |
| 4,018,547 A | 4/1977 | Rogen |
| 4,048,551 A | 9/1977 | Bosik |
| 4,121,282 A | 10/1978 | Ohsawa |
| 4,146,029 A | 3/1979 | Elinwood |
| 4,193,397 A | 3/1980 | Tucker et al. |
| 4,268,173 A | 5/1981 | Barnard et al. |

(Continued)

FOREIGN PATENT DOCUMENTS

| | | |
|---|---|---|
| EP | 0455455 | 11/1991 |
| EP | 0465708 | 1/1992 |

(Continued)

OTHER PUBLICATIONS

PCT Application No. PCT/US2010/032861, International Preliminary Report on Patentability and Written Opinion of the International Searching Authority mailed Nov. 10, 2011.

(Continued)

*Primary Examiner* — Larry D Riggs, II

(74) *Attorney, Agent, or Firm* — Jackson & Co., LLP

(57) ABSTRACT

Methods and devices to generate a tool for testing, simulating and/or modifying a closed loop control algorithm are provided. Embodiments include receiving glucose data for a predetermined time period, determining a variation in the glucose level based on the received glucose data, filtering a received glucose data based on the determined variation, substituting a negative change in the glucose data value with a predetermined value to generate a sequence of modified glucose values, and integrating the sequence of modified glucose values to determine an uncontrolled blood glucose excursion condition.

20 Claims, 3 Drawing Sheets

U.S. PATENT DOCUMENTS

| | | | |
|---|---|---|---|
| 4,288,793 A | 9/1981 | Lotscher |
| 4,309,156 A | 1/1982 | Gonner et al. |
| 4,362,052 A | 12/1982 | Heath et al. |
| 4,401,122 A | 8/1983 | Clark, Jr. |
| 4,439,197 A | 3/1984 | Honda et al. |
| 4,441,968 A | 4/1984 | Emmer et al. |
| 4,447,224 A | 5/1984 | DeCant, Jr. et al. |
| 4,458,686 A | 7/1984 | Clark, Jr. |
| 4,467,811 A | 8/1984 | Clark, Jr. |
| 4,472,113 A | 9/1984 | Rogen |
| 4,474,309 A | 10/1984 | Solomon |
| 4,486,190 A | 12/1984 | Reinicke |
| 4,494,950 A | 1/1985 | Fischell |
| 4,512,348 A | 4/1985 | Uchigaki et al. |
| 4,524,343 A | 6/1985 | Morgan et al. |
| 4,529,401 A | 7/1985 | Leslie et al. |
| 4,531,235 A | 7/1985 | Brusen |
| 4,562,751 A | 1/1986 | Nason et al. |
| 4,563,249 A | 1/1986 | Hale |
| 4,570,492 A | 2/1986 | Walsh |
| 4,573,994 A | 3/1986 | Fischell et al. |
| 4,574,809 A | 3/1986 | Talish et al. |
| 4,633,878 A | 1/1987 | Bombardieri |
| 4,678,408 A | 7/1987 | Nason et al. |
| 4,685,903 A | 8/1987 | Cable et al. |
| 4,686,624 A | 8/1987 | Blum et al. |
| 4,736,748 A | 4/1988 | Nakamura et al. |
| 4,755,173 A | 7/1988 | Konopka et al. |
| 4,811,564 A | 3/1989 | Palmer |
| 4,850,959 A | 7/1989 | Findl |
| 4,851,827 A | 7/1989 | Nicholas |
| 4,866,396 A | 9/1989 | Tamura |
| 4,883,409 A | 11/1989 | Strohmeier et al. |
| 4,890,621 A | 1/1990 | Hakky |
| 4,953,552 A | 9/1990 | DeMarzo |
| 4,976,590 A | 12/1990 | Baldwin |
| 4,979,509 A | 12/1990 | Hakky |
| 4,984,581 A | 1/1991 | Stice |
| 5,004,532 A | 4/1991 | Hale et al. |
| 5,012,667 A | 5/1991 | Kruse |
| 5,019,974 A | 5/1991 | Beckers |
| 5,036,861 A | 8/1991 | Sembrowich et al. |
| 5,051,880 A | 9/1991 | Harm et al. |
| 5,061,914 A | 10/1991 | Bush et al. |
| 5,078,683 A | 1/1992 | Sancoff et al. |
| 5,079,920 A | 1/1992 | Whitehead et al. |
| 5,081,421 A | 1/1992 | Miller et al. |
| 5,101,814 A | 4/1992 | Palti |
| 5,124,661 A | 6/1992 | Zelin et al. |
| 5,139,023 A | 8/1992 | Stanley et al. |
| 5,155,695 A * | 10/1992 | Stein ............................ 702/178 |
| 5,190,041 A | 3/1993 | Palti |
| 5,205,819 A | 4/1993 | Ross et al. |
| 5,207,666 A | 5/1993 | Idriss et al. |
| 5,211,371 A | 5/1993 | Coffee |
| 5,211,626 A | 5/1993 | Frank et al. |
| 5,223,822 A | 6/1993 | Stommes et al. |
| 5,262,305 A | 11/1993 | Heller et al. |
| 5,264,104 A | 11/1993 | Gregg et al. |
| 5,267,026 A * | 11/1993 | Kawahara et al. ......... 348/223.1 |
| 5,278,997 A | 1/1994 | Martin |
| 5,284,423 A | 2/1994 | Holdsworth et al. |
| 5,284,425 A | 2/1994 | Holtermann et al. |
| 5,291,614 A | 3/1994 | Baker et al. |
| 5,291,887 A | 3/1994 | Stanley et al. |
| 5,320,725 A | 6/1994 | Gregg et al. |
| 5,324,599 A | 6/1994 | Oyama et al. |
| 5,325,280 A | 6/1994 | Tortola et al. |
| 5,349,852 A | 9/1994 | Kamen et al. |
| 5,356,786 A | 10/1994 | Heller et al. |
| 5,366,292 A | 11/1994 | Voss |
| 5,368,028 A | 11/1994 | Palti |
| 5,371,687 A | 12/1994 | Holmes, II et al. |
| 5,372,133 A | 12/1994 | Hogen Esch |
| 5,376,070 A | 12/1994 | Purvis et al. |
| 5,382,331 A | 1/1995 | Banks |
| 5,390,671 A | 2/1995 | Lord et al. |
| 5,391,250 A | 2/1995 | Cheney, II et al. |
| 5,398,681 A | 3/1995 | Kuperschmidt |
| 5,404,585 A | 4/1995 | Vimpari et al. |
| 5,406,301 A | 4/1995 | Ravid |
| 5,445,611 A | 8/1995 | Eppstein et al. |
| 5,448,992 A | 9/1995 | Kuperschmidt |
| 5,458,140 A | 10/1995 | Eppstein et al. |
| 5,469,025 A | 11/1995 | Kanemori et al. |
| 5,479,486 A | 12/1995 | Saji |
| 5,494,562 A | 2/1996 | Maley et al. |
| 5,497,772 A | 3/1996 | Schulman et al. |
| 5,505,713 A | 4/1996 | Van Antwerp |
| 5,507,288 A | 4/1996 | Bocker et al. |
| 5,515,390 A | 5/1996 | Benton |
| 5,517,434 A | 5/1996 | Hanson et al. |
| 5,526,844 A | 6/1996 | Kamen et al. |
| 5,533,389 A | 7/1996 | Kamen et al. |
| 5,543,678 A | 8/1996 | Hoiberg |
| 5,559,528 A | 9/1996 | Ravid |
| 5,568,400 A | 10/1996 | Stark et al. |
| 5,568,806 A | 10/1996 | Cheney, II et al. |
| 5,575,770 A | 11/1996 | Melsky et al. |
| 5,576,535 A | 11/1996 | Oosterwijk et al. |
| 5,586,553 A | 12/1996 | Halili et al. |
| 5,593,852 A | 1/1997 | Heller et al. |
| 5,594,906 A | 1/1997 | Holmes, II et al. |
| 5,596,261 A | 1/1997 | Suyama |
| 5,601,435 A | 2/1997 | Quy |
| 5,604,404 A | 2/1997 | Sahara |
| 5,615,671 A | 4/1997 | Schoonen et al. |
| 5,622,413 A | 4/1997 | Kim et al. |
| 5,622,482 A | 4/1997 | Lee |
| 5,640,954 A | 6/1997 | Pfeiffer et al. |
| 5,645,709 A | 7/1997 | Birch et al. |
| 5,660,163 A | 8/1997 | Schulman et al. |
| 5,661,643 A | 8/1997 | Blakely et al. |
| 5,662,461 A | 9/1997 | Ono |
| 5,665,222 A | 9/1997 | Heller et al. |
| 5,671,301 A | 9/1997 | Kuperschmidt |
| 5,685,844 A | 11/1997 | Marttila |
| 5,695,949 A | 12/1997 | Galen et al. |
| 5,703,928 A | 12/1997 | Galloway et al. |
| 5,707,502 A | 1/1998 | McCaffrey et al. |
| 5,708,247 A | 1/1998 | McAleer et al. |
| 5,711,861 A | 1/1998 | Ward et al. |
| 5,711,868 A | 1/1998 | Maley et al. |
| 5,722,397 A | 3/1998 | Eppstein |
| 5,738,220 A | 4/1998 | Geszler |
| 5,741,211 A | 4/1998 | Renirie et al. |
| 5,748,872 A | 5/1998 | Norman |
| 5,759,510 A | 6/1998 | Pillai |
| 5,771,890 A | 6/1998 | Tamada |
| 5,774,254 A | 6/1998 | Berlin |
| 5,786,439 A | 7/1998 | Van Antwerp et al. |
| 5,790,297 A | 8/1998 | Berlin |
| 5,791,344 A * | 8/1998 | Schulman et al. ............ 600/347 |
| 5,812,102 A | 9/1998 | Sprole et al. |
| 5,814,020 A | 9/1998 | Gross |
| 5,814,599 A | 9/1998 | Mitragotri et al. |
| 5,815,303 A | 9/1998 | Berlin |
| 5,822,715 A | 10/1998 | Worthington et al. |
| 5,825,488 A | 10/1998 | Kohl et al. |
| 5,848,990 A | 12/1998 | Cirelli et al. |
| 5,851,197 A | 12/1998 | Marano et al. |
| 5,856,631 A | 1/1999 | Julien |
| 5,858,001 A | 1/1999 | Tsals et al. |
| 5,873,026 A | 2/1999 | Reames |
| 5,875,417 A | 2/1999 | Golden |
| 5,885,211 A | 3/1999 | Eppstein et al. |
| 5,899,855 A | 5/1999 | Brown |
| 5,913,833 A | 6/1999 | Elstrom et al. |
| 5,918,603 A | 7/1999 | Brown |
| 5,919,167 A | 7/1999 | Mulhauser |
| 5,923,512 A | 7/1999 | Brownlow et al. |
| 5,931,814 A | 8/1999 | Alex et al. |
| 5,947,921 A | 9/1999 | Johnson et al. |
| 5,948,512 A | 9/1999 | Kubota et al. |
| 5,951,582 A | 9/1999 | Thorne et al. |
| 5,951,836 A | 9/1999 | McAleer et al. |
| 5,954,643 A | 9/1999 | Van Antwerp et al. |

| Patent No. | Date | Inventor |
|---|---|---|
| 5,965,380 A | 10/1999 | Heller et al. |
| 5,968,011 A | 10/1999 | Larsen et al. |
| 5,971,922 A | 10/1999 | Arita et al. |
| 5,972,199 A | 10/1999 | Heller et al. |
| 5,993,411 A | 11/1999 | Choi |
| 5,994,878 A | 11/1999 | Ostergaard et al. |
| 5,997,501 A | 12/1999 | Gross et al. |
| 6,001,067 A | 12/1999 | Shults et al. |
| 6,002,961 A | 12/1999 | Mitragotri et al. |
| 6,011,486 A | 1/2000 | Casey |
| 6,014,577 A | 1/2000 | Henning et al. |
| 6,017,328 A | 1/2000 | Fischell et al. |
| 6,018,678 A | 1/2000 | Mitragotri et al. |
| 6,023,629 A | 2/2000 | Tamada |
| 6,024,539 A | 2/2000 | Blomquist et al. |
| 6,026,320 A | 2/2000 | Carlson et al. |
| 6,027,459 A | 2/2000 | Shain et al. |
| 6,027,496 A | 2/2000 | Loomis et al. |
| 6,027,692 A | 2/2000 | Galen et al. |
| 6,032,059 A | 2/2000 | Henning et al. |
| 6,041,253 A | 3/2000 | Kost et al. |
| 6,041,665 A | 3/2000 | Hussain |
| 6,059,546 A | 5/2000 | Brenan et al. |
| 6,063,039 A | 5/2000 | Cunningham et al. |
| 6,064,368 A | 5/2000 | Kang |
| 6,066,243 A | 5/2000 | Anderson et al. |
| 6,067,017 A | 5/2000 | Stewart et al. |
| 6,067,463 A | 5/2000 | Jeng et al. |
| 6,071,249 A | 6/2000 | Cunningham et al. |
| 6,071,251 A | 6/2000 | Cunningham et al. |
| 6,073,031 A | 6/2000 | Helstab et al. |
| 6,077,660 A | 6/2000 | Wong et al. |
| 6,081,104 A | 6/2000 | Kern |
| 6,083,710 A | 7/2000 | Heller et al. |
| 6,085,871 A | 7/2000 | Karamata |
| 6,086,575 A | 7/2000 | Mejslov |
| 6,091,975 A | 7/2000 | Daddona et al. |
| 6,093,156 A | 7/2000 | Cunningham et al. |
| 6,093,172 A | 7/2000 | Funderburk et al. |
| 6,103,033 A | 8/2000 | Say et al. |
| 6,120,676 A | 9/2000 | Heller et al. |
| 6,121,009 A | 9/2000 | Heller et al. |
| 6,129,823 A | 10/2000 | Hughes et al. |
| 6,132,371 A | 10/2000 | Dempsey et al. |
| 6,134,461 A | 10/2000 | Say et al. |
| 6,142,939 A | 11/2000 | Eppstein et al. |
| 6,143,164 A | 11/2000 | Heller et al. |
| 6,144,303 A | 11/2000 | Federman |
| 6,144,869 A | 11/2000 | Berner et al. |
| 6,144,922 A | 11/2000 | Douglas et al. |
| 6,147,342 A | 11/2000 | Kucher |
| 6,154,855 A | 11/2000 | Norman |
| 6,155,992 A | 12/2000 | Henning et al. |
| 6,157,442 A | 12/2000 | Raskas |
| 6,160,449 A | 12/2000 | Klomsdorf et al. |
| 6,162,202 A | 12/2000 | Sicurelli et al. |
| 6,162,611 A | 12/2000 | Heller et al. |
| 6,164,284 A | 12/2000 | Schulman et al. |
| 6,173,160 B1 | 1/2001 | Liimatainen |
| 6,175,752 B1 | 1/2001 | Say et al. |
| 6,180,416 B1 | 1/2001 | Kurnik et al. |
| 6,185,452 B1 | 2/2001 | Schulman et al. |
| 6,186,982 B1 | 2/2001 | Gross et al. |
| 6,201,980 B1 | 3/2001 | Darrow et al. |
| 6,203,288 B1 | 3/2001 | Kottke |
| 6,206,841 B1 | 3/2001 | Cunningham et al. |
| 6,208,894 B1 | 3/2001 | Schulman et al. |
| 6,212,416 B1 | 4/2001 | Ward et al. |
| 6,215,206 B1 | 4/2001 | Chitayat |
| 6,222,514 B1 | 4/2001 | DeLuca |
| 6,228,100 B1 | 5/2001 | Schraga |
| 6,232,370 B1 | 5/2001 | Kubota et al. |
| 6,233,471 B1 | 5/2001 | Berner et al. |
| 6,233,539 B1 | 5/2001 | Brown |
| 6,242,961 B1 | 6/2001 | Liu et al. |
| 6,245,060 B1 | 6/2001 | Loomis et al. |
| 6,248,067 B1 | 6/2001 | Causey, III et al. |
| 6,262,708 B1 | 7/2001 | Chu |
| 6,272,364 B1 | 8/2001 | Kurnik |
| 6,278,425 B1 | 8/2001 | DeLuca |
| 6,280,587 B1 | 8/2001 | Matsumoto |
| 6,283,926 B1 | 9/2001 | Cunningham et al. |
| 6,283,951 B1 | 9/2001 | Flaherty et al. |
| 6,284,478 B1 | 9/2001 | Heller et al. |
| 6,288,653 B1 | 9/2001 | Shih |
| 6,293,925 B1 | 9/2001 | Safabash et al. |
| 6,295,506 B1 | 9/2001 | Heinonen et al. |
| 6,298,254 B2 | 10/2001 | Tamada |
| 6,298,255 B1 | 10/2001 | Cordero et al. |
| 6,299,578 B1 | 10/2001 | Kurnik et al. |
| 6,301,499 B1 | 10/2001 | Carlson et al. |
| 6,306,104 B1 | 10/2001 | Cunningham et al. |
| 6,309,351 B1 | 10/2001 | Kurnik et al. |
| 6,312,888 B1 | 11/2001 | Wong et al. |
| 6,315,721 B2 | 11/2001 | Schulman et al. |
| 6,326,160 B1 | 12/2001 | Dunn et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,341,232 B1 | 1/2002 | Conn et al. |
| 6,356,776 B1 | 3/2002 | Berner et al. |
| 6,360,888 B1 | 3/2002 | McIvor et al. |
| 6,366,793 B1 | 4/2002 | Bell et al. |
| 6,368,141 B1 | 4/2002 | Van Antwerp et al. |
| 6,368,274 B1 | 4/2002 | Van Antwerp et al. |
| 6,372,371 B1 | 4/2002 | Iarochenko et al. |
| 6,375,344 B1 | 4/2002 | Hanson et al. |
| 6,375,638 B2 | 4/2002 | Nason et al. |
| 6,377,894 B1 | 4/2002 | Deweese et al. |
| 6,379,301 B1 | 4/2002 | Worthington et al. |
| 6,381,496 B1 | 4/2002 | Meadows et al. |
| 6,393,318 B1 | 5/2002 | Conn et al. |
| 6,403,944 B1 | 6/2002 | MacKenzie et al. |
| 6,405,066 B1 | 6/2002 | Essenpreis et al. |
| 6,408,402 B1 | 6/2002 | Norman |
| 6,417,074 B2 | 7/2002 | Kopley et al. |
| 6,418,332 B1 | 7/2002 | Mastrototaro et al. |
| 6,419,642 B1 | 7/2002 | Marchitto et al. |
| 6,425,829 B1 | 7/2002 | Julien |
| 6,427,088 B1 | 7/2002 | Bowman, IV et al. |
| 6,432,585 B1 | 8/2002 | Kawakami et al. |
| 6,437,379 B2 | 8/2002 | Kopley et al. |
| 6,438,385 B1 | 8/2002 | Heinonen et al. |
| 6,438,414 B1 | 8/2002 | Conn et al. |
| 6,442,413 B1 | 8/2002 | Silver |
| 6,445,374 B2 | 9/2002 | Albert et al. |
| 6,461,329 B1 | 10/2002 | Van Antwerp et al. |
| 6,462,162 B2 | 10/2002 | Van Antwerp et al. |
| 6,464,848 B1 | 10/2002 | Matsumoto |
| 6,466,807 B1 | 10/2002 | Dobson et al. |
| 6,466,810 B1 | 10/2002 | Ward et al. |
| 6,468,222 B1 | 10/2002 | Mault et al. |
| 6,471,980 B2 | 10/2002 | Sirhan et al. |
| 6,472,991 B1 | 10/2002 | Schulman et al. |
| 6,475,196 B1 | 11/2002 | Vachon |
| 6,478,736 B1 | 11/2002 | Mault |
| 6,480,730 B2 | 11/2002 | Darrow et al. |
| 6,482,158 B2 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,485,138 B1 | 11/2002 | Kubota et al. |
| 6,485,461 B1 | 11/2002 | Mason et al. |
| 6,485,465 B2 | 11/2002 | Morberg et al. |
| 6,492,180 B2 | 12/2002 | Brown et al. |
| 6,498,043 B1 | 12/2002 | Schulman et al. |
| 6,506,168 B1 | 1/2003 | Fathallah et al. |
| 6,513,532 B2 | 2/2003 | Mault et al. |
| 6,514,460 B1 | 2/2003 | Fendrock |
| 6,514,689 B2 | 2/2003 | Han et al. |
| 6,514,718 B2 | 2/2003 | Heller et al. |
| 6,522,530 B2 | 2/2003 | Bang |
| 6,525,330 B2 | 2/2003 | Paolini et al. |
| 6,526,298 B1 | 2/2003 | Khalil et al. |
| 6,529,772 B2 | 3/2003 | Carlson et al. |
| 6,530,915 B1 | 3/2003 | Eppstein et al. |
| 6,535,753 B1 | 3/2003 | Raskas |
| 6,537,243 B1 | 3/2003 | Henning et al. |

| Patent | Date | Inventor |
|---|---|---|
| 6,540,675 B2 | 4/2003 | Aceti et al. |
| 6,540,891 B1 | 4/2003 | Stewart et al. |
| 6,543,224 B1 | 4/2003 | Barooah |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 | 5/2003 | Say et al. |
| 6,565,738 B1 | 5/2003 | Henning et al. |
| 6,569,157 B1 | 5/2003 | Shain et al. |
| 6,571,128 B2 | 5/2003 | Lebel et al. |
| 6,571,200 B1 | 5/2003 | Mault |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,582,393 B2 | 6/2003 | Sage, Jr. |
| 6,585,644 B2 | 7/2003 | Lebel et al. |
| 6,586,971 B1 | 7/2003 | Naffziger et al. |
| 6,587,705 B1 | 7/2003 | Kim et al. |
| 6,589,229 B1 | 7/2003 | Connelly et al. |
| 6,594,514 B2 | 7/2003 | Berner et al. |
| 6,595,919 B2 | 7/2003 | Berner et al. |
| 6,596,016 B1 | 7/2003 | Vreman et al. |
| 6,600,997 B2 | 7/2003 | Deweese et al. |
| 6,602,469 B1 | 8/2003 | Maus et al. |
| 6,607,509 B2 | 8/2003 | Bobroff et al. |
| 6,610,012 B2 | 8/2003 | Mault |
| 6,612,306 B1 | 9/2003 | Mault |
| 6,615,061 B1 | 9/2003 | Khalil et al. |
| 6,615,074 B2 | 9/2003 | Mickle et al. |
| 6,618,603 B2 | 9/2003 | Varalli et al. |
| 6,620,106 B2 | 9/2003 | Mault |
| 6,623,501 B2 | 9/2003 | Heller et al. |
| 6,629,934 B2 | 10/2003 | Mault et al. |
| 6,633,095 B1 | 10/2003 | Swope et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,645,142 B2 | 11/2003 | Braig et al. |
| 6,648,821 B2 | 11/2003 | Lebel et al. |
| 6,650,064 B2 | 11/2003 | Guthrie et al. |
| 6,653,091 B1 | 11/2003 | Dunn et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,980 B2 | 12/2003 | Morberg et al. |
| 6,668,196 B1 | 12/2003 | Villegas et al. |
| 6,669,663 B1 | 12/2003 | Thompson |
| 6,669,669 B2 | 12/2003 | Flaherty et al. |
| 6,670,806 B2 | 12/2003 | Wendt et al. |
| 6,679,841 B2 | 1/2004 | Bojan et al. |
| 6,687,522 B2 | 2/2004 | Tamada |
| 6,687,546 B2 | 2/2004 | Lebel et al. |
| 6,692,457 B2 | 2/2004 | Flaherty |
| 6,694,191 B2 | 2/2004 | Starkweather et al. |
| 6,695,885 B2 | 2/2004 | Schulman et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,728,560 B2 | 4/2004 | Kollias et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,736,777 B2 | 5/2004 | Kim et al. |
| 6,736,797 B1 | 5/2004 | Larsen et al. |
| 6,738,654 B2 | 5/2004 | Sohrab |
| 6,740,059 B2 | 5/2004 | Flaherty |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,749,587 B2 | 6/2004 | Flaherty |
| 6,752,785 B2 | 6/2004 | Van Antwerp et al. |
| 6,752,787 B1 | 6/2004 | Causey, III et al. |
| 6,758,810 B2 | 7/2004 | Lebel et al. |
| 6,764,581 B1 | 7/2004 | Forrow et al. |
| 6,768,425 B2 | 7/2004 | Flaherty et al. |
| 6,770,030 B1 | 8/2004 | Schaupp et al. |
| 6,770,729 B2 | 8/2004 | Van Antwerp |
| 6,773,563 B2 | 8/2004 | Matsumoto |
| 6,779,984 B2 | 8/2004 | Lilie et al. |
| 6,789,195 B1 | 9/2004 | Prihoda et al. |
| 6,790,178 B1 | 9/2004 | Mault et al. |
| 6,794,195 B2 | 9/2004 | Colvin, Jr. |
| 6,799,861 B2 | 10/2004 | Naghi et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,816,742 B2 | 11/2004 | Kim et al. |
| 6,818,348 B1 | 11/2004 | Venkatesan et al. |
| 6,830,558 B2 | 12/2004 | Flaherty et al. |
| 6,832,114 B1 | 12/2004 | Whitehurst et al. |
| 6,833,540 B2 | 12/2004 | MacKenzie et al. |
| 6,835,553 B2 | 12/2004 | Han et al. |
| 6,837,858 B2 | 1/2005 | Cunningham et al. |
| 6,839,596 B2 | 1/2005 | Nelson et al. |
| 6,840,912 B2 | 1/2005 | Kloepfer et al. |
| 6,849,237 B2 | 2/2005 | Housefield et al. |
| 6,850,790 B2 | 2/2005 | Berner et al. |
| 6,859,831 B1 | 2/2005 | Gelvin et al. |
| 6,862,465 B2 | 3/2005 | Shults et al. |
| 6,872,200 B2 | 3/2005 | Mann et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,893,396 B2 | 5/2005 | Schulze et al. |
| 6,895,265 B2 | 5/2005 | Silver |
| 6,898,451 B2 | 5/2005 | Wuori |
| 6,899,683 B2 | 5/2005 | Mault et al. |
| 6,899,684 B2 | 5/2005 | Mault et al. |
| 6,904,301 B2 | 6/2005 | Raskas |
| 6,907,127 B1 | 6/2005 | Kravitz et al. |
| 6,908,535 B2 | 6/2005 | Rankin et al. |
| 6,916,159 B2 | 7/2005 | Rush et al. |
| 6,918,874 B1 | 7/2005 | Hatch et al. |
| 6,922,576 B2 | 7/2005 | Raskas |
| 6,922,578 B2 | 7/2005 | Eppstein et al. |
| 6,923,764 B2 | 8/2005 | Aceti et al. |
| 6,927,749 B1 | 8/2005 | Klemm |
| 6,931,327 B2 | 8/2005 | Goode, Jr. et al. |
| 6,936,029 B2 | 8/2005 | Mann et al. |
| 6,949,816 B2 | 9/2005 | Brown et al. |
| 6,950,708 B2 | 9/2005 | Bowman, IV et al. |
| 6,952,603 B2 | 10/2005 | Gerber et al. |
| 6,955,650 B2 | 10/2005 | Mault et al. |
| 6,958,129 B2 | 10/2005 | Galen et al. |
| 6,958,705 B2 | 10/2005 | Lebel et al. |
| 6,960,192 B1 | 11/2005 | Flaherty et al. |
| 6,961,448 B2 | 11/2005 | Nichols et al. |
| 6,974,437 B2 | 12/2005 | Lebel et al. |
| 6,979,326 B2 | 12/2005 | Mann et al. |
| 6,990,366 B2 | 1/2006 | Say et al. |
| 6,990,372 B2 | 1/2006 | Perron et al. |
| 6,997,911 B2 | 2/2006 | Klitmose |
| 6,997,920 B2 | 2/2006 | Mann et al. |
| 6,999,810 B2 | 2/2006 | Berner et al. |
| 7,003,340 B2 | 2/2006 | Say et al. |
| 7,003,341 B2 | 2/2006 | Say et al. |
| 7,005,857 B2 | 2/2006 | Stiene et al. |
| 7,006,858 B2 | 2/2006 | Silver et al. |
| 7,010,356 B2 | 3/2006 | Jog et al. |
| 7,011,630 B2 | 3/2006 | Desai et al. |
| 7,018,360 B2 | 3/2006 | Flaherty et al. |
| 7,020,508 B2 | 3/2006 | Stirovic et al. |
| 7,024,245 B2 | 4/2006 | Lebel et al. |
| 7,024,249 B2 | 4/2006 | Weisner et al. |

| Patent | Date | Inventor |
|---|---|---|
| 7,025,743 B2 | 4/2006 | Mann et al. |
| 7,029,444 B2 | 4/2006 | Shin et al. |
| 7,029,455 B2 | 4/2006 | Flaherty |
| 7,034,677 B2 | 4/2006 | Steinthal et al. |
| 7,041,468 B2 | 5/2006 | Drucker et al. |
| 7,043,287 B1 | 5/2006 | Khalil et al. |
| 7,052,251 B2 | 5/2006 | Nason et al. |
| 7,058,437 B2 | 6/2006 | Buse et al. |
| 7,067,498 B2 | 6/2006 | Wolf et al. |
| 7,070,591 B2 | 7/2006 | Adams et al. |
| 7,072,738 B2 | 7/2006 | Bonney et al. |
| 7,074,307 B2 | 7/2006 | Simpson et al. |
| 7,077,328 B2 | 7/2006 | Krishnaswamy et al. |
| 7,079,901 B1 | 7/2006 | Loftin et al. |
| 7,081,195 B2 | 7/2006 | Simpson et al. |
| 7,083,593 B2 | 8/2006 | Stultz |
| 7,086,277 B2 | 8/2006 | Tess et al. |
| 7,092,762 B1 | 8/2006 | Loftin et al. |
| 7,097,983 B2 | 8/2006 | Markovsky et al. |
| 7,098,803 B2 | 8/2006 | Mann et al. |
| 7,108,711 B2 | 9/2006 | Vogel et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,123,206 B2 | 10/2006 | Hess et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,136,704 B2 | 11/2006 | Schulman |
| 7,137,964 B2 | 11/2006 | Flaherty |
| 7,144,384 B2 | 12/2006 | Gorman et al. |
| 7,149,581 B2 | 12/2006 | Goedeke |
| 7,153,212 B1 | 12/2006 | Karten et al. |
| 7,154,398 B2 | 12/2006 | Chen et al. |
| 7,163,511 B2 | 1/2007 | Conn et al. |
| 7,167,818 B2 | 1/2007 | Brown |
| 7,171,274 B2 | 1/2007 | Starkweather et al. |
| 7,181,261 B2 | 2/2007 | Silver et al. |
| 7,186,566 B2 | 3/2007 | Qian |
| 7,186,791 B2 | 3/2007 | Bruno et al. |
| 7,192,450 B2 | 3/2007 | Brauker et al. |
| 7,193,521 B2 | 3/2007 | Morberg et al. |
| 7,198,603 B2 | 4/2007 | Penner et al. |
| 7,202,734 B1 | 4/2007 | Raab |
| 7,205,409 B2 | 4/2007 | Pei et al. |
| 7,208,119 B1 | 4/2007 | Kurtock et al. |
| 7,211,048 B1 | 5/2007 | Najafi et al. |
| 7,218,017 B1 | 5/2007 | Chitayet et al. |
| 7,225,535 B2 | 6/2007 | Feldman et al. |
| 7,226,278 B2 | 6/2007 | Nason et al. |
| 7,226,442 B2 | 6/2007 | Sheppard, Jr. et al. |
| 7,226,978 B2 | 6/2007 | Tapsak et al. |
| 7,258,666 B2 | 8/2007 | Brown |
| 7,266,400 B2 | 9/2007 | Fine et al. |
| 7,267,665 B2 | 9/2007 | Steil et al. |
| 7,276,029 B2 | 10/2007 | Goode, Jr. et al. |
| 7,283,867 B2 | 10/2007 | Strother et al. |
| 7,291,497 B2 | 11/2007 | Holmes et al. |
| 7,299,080 B2 | 11/2007 | Acosta et al. |
| 7,303,549 B2 | 12/2007 | Flaherty et al. |
| 7,310,544 B2 | 12/2007 | Brister et al. |
| 7,323,091 B1 | 1/2008 | Gillette et al. |
| 7,324,949 B2 | 1/2008 | Bristol et al. |
| 7,343,188 B2 | 3/2008 | Sohrab |
| 7,364,592 B2 | 4/2008 | Carr-Brendel et al. |
| 7,366,556 B2 | 4/2008 | Brister et al. |
| 7,371,247 B2 | 5/2008 | Boecker et al. |
| 7,379,765 B2 | 5/2008 | Petisce et al. |
| 7,424,318 B2 | 9/2008 | Brister et al. |
| 7,436,511 B2 * | 10/2008 | Ruchti et al. .......... 356/326 |
| 7,460,898 B2 | 12/2008 | Brister et al. |
| 7,467,003 B2 | 12/2008 | Brister et al. |
| 7,471,972 B2 | 12/2008 | Rhodes et al. |
| 7,480,138 B2 | 1/2009 | Kogan et al. |
| 7,494,465 B2 | 2/2009 | Brister et al. |
| 7,497,827 B2 | 3/2009 | Brister et al. |
| 7,510,526 B2 | 3/2009 | Merry et al. |
| 7,519,408 B2 | 4/2009 | Rasdal et al. |
| 7,583,190 B2 | 9/2009 | Reggiardo et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,613,491 B2 | 11/2009 | Boock et al. |
| 7,615,007 B2 | 11/2009 | Shults et al. |
| 7,620,437 B2 | 11/2009 | Reggiardo |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,679,407 B2 | 3/2010 | Reggiardo |
| 7,711,402 B2 | 5/2010 | Shults et al. |
| 7,713,574 B2 | 5/2010 | Brister et al. |
| 7,715,893 B2 | 5/2010 | Kamath et al. |
| 7,756,561 B2 | 7/2010 | Reggiardo et al. |
| 7,768,408 B2 | 8/2010 | Reggiardo et al. |
| 7,778,795 B2 | 8/2010 | Fukushima et al. |
| 7,850,621 B2 | 12/2010 | Briggs et al. |
| 7,882,611 B2 | 2/2011 | Shah et al. |
| 7,911,010 B2 | 3/2011 | Stetter |
| 7,954,385 B2 | 6/2011 | Raisanen |
| 8,260,393 B2 * | 9/2012 | Kamath et al. .......... 600/347 |
| 2001/0016682 A1 | 8/2001 | Berner et al. |
| 2001/0016683 A1 | 8/2001 | Darrow et al. |
| 2001/0016710 A1 | 8/2001 | Nason et al. |
| 2001/0020124 A1 | 9/2001 | Tamada |
| 2001/0023095 A1 | 9/2001 | Kopley et al. |
| 2001/0024864 A1 | 9/2001 | Kopley et al. |
| 2001/0029340 A1 | 10/2001 | Mault et al. |
| 2001/0034502 A1 | 10/2001 | Moberg et al. |
| 2001/0034617 A1 | 10/2001 | Kimata |
| 2001/0037060 A1 | 11/2001 | Thompson et al. |
| 2001/0037069 A1 | 11/2001 | Carlson et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0049470 A1 | 12/2001 | Mault et al. |
| 2001/0053891 A1 | 12/2001 | Ackley |
| 2001/0056255 A1 | 12/2001 | Kost et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0019022 A1 | 2/2002 | Dunn et al. |
| 2002/0019612 A1 | 2/2002 | Watanabe et al. |
| 2002/0026937 A1 | 3/2002 | Mault |
| 2002/0027164 A1 | 3/2002 | Mault et al. |
| 2002/0028995 A1 | 3/2002 | Mault |
| 2002/0032374 A1 | 3/2002 | Holker et al. |
| 2002/0040208 A1 | 4/2002 | Flaherty et al. |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0065682 A1 | 5/2002 | Goldenberg |
| 2002/0068858 A1 | 6/2002 | Braig et al. |
| 2002/0077765 A1 | 6/2002 | Mault |
| 2002/0077766 A1 | 6/2002 | Mault |
| 2002/0087056 A1 | 7/2002 | Aceti et al. |
| 2002/0091312 A1 | 7/2002 | Berner et al. |
| 2002/0091454 A1 | 7/2002 | Vasko |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0118090 A1 | 8/2002 | Park et al. |
| 2002/0119711 A1 | 8/2002 | Van Antwerp et al. |
| 2002/0124017 A1 | 9/2002 | Mault |
| 2002/0133378 A1 | 9/2002 | Mault et al. |
| 2002/0161286 A1 | 10/2002 | Gerber et al. |
| 2002/0169394 A1 | 11/2002 | Eppstein et al. |
| 2002/0169439 A1 | 11/2002 | Flaherty et al. |
| 2002/0177764 A1 | 11/2002 | Sohrab |
| 2002/0193679 A1 | 12/2002 | Malave et al. |

| | | | | | | |
|---|---|---|---|---|---|---|
| 2003/0009133 A1 | 1/2003 | Ramey | | 2004/0072357 A1 | 4/2004 | Stiene et al. |
| 2003/0023182 A1 | 1/2003 | Mault et al. | | 2004/0073095 A1 | 4/2004 | Causey, III et al. |
| 2003/0023317 A1 | 1/2003 | Brauker et al. | | 2004/0085215 A1 | 5/2004 | Moberg et al. |
| 2003/0028089 A1 | 2/2003 | Galley et al. | | 2004/0096959 A1 | 5/2004 | Stiene et al. |
| 2003/0028120 A1 | 2/2003 | Mault et al. | | 2004/0100376 A1 | 5/2004 | Lye et al. |
| 2003/0032868 A1 | 2/2003 | Graskov et al. | | 2004/0106858 A1 | 6/2004 | Say et al. |
| 2003/0032874 A1 | 2/2003 | Rhodes et al. | | 2004/0106859 A1 | 6/2004 | Say et al. |
| 2003/0040683 A1 | 2/2003 | Rule et al. | | 2004/0106860 A1 | 6/2004 | Say et al. |
| 2003/0050546 A1 | 3/2003 | Desai et al. | | 2004/0108226 A1 | 6/2004 | Polychronakos et al. |
| 2003/0050575 A1 | 3/2003 | Diermann et al. | | 2004/0115067 A1 | 6/2004 | Rush et al. |
| 2003/0055380 A1 | 3/2003 | Flaherty et al. | | 2004/0116847 A1 | 6/2004 | Wall |
| 2003/0060692 A1 | 3/2003 | Ruchti et al. | | 2004/0116866 A1 | 6/2004 | Gorman et al. |
| 2003/0060765 A1 | 3/2003 | Campbell et al. | | 2004/0122353 A1 | 6/2004 | Shahmirian et al. |
| 2003/0065254 A1 | 4/2003 | Schulman et al. | | 2004/0132220 A1 | 7/2004 | Fish |
| 2003/0065257 A1 | 4/2003 | Mault et al. | | 2004/0133092 A1 | 7/2004 | Kain |
| 2003/0065273 A1 | 4/2003 | Mault et al. | | 2004/0152622 A1 | 8/2004 | Keith et al. |
| 2003/0065274 A1 | 4/2003 | Mault et al. | | 2004/0153032 A1 | 8/2004 | Garribotto et al. |
| 2003/0065275 A1 | 4/2003 | Mault et al. | | 2004/0158137 A1 | 8/2004 | Eppstein et al. |
| 2003/0065308 A1 | 4/2003 | Lebel et al. | | 2004/0162473 A1 | 8/2004 | Sohrab |
| 2003/0078560 A1 | 4/2003 | Miller et al. | | 2004/0164961 A1 | 8/2004 | Bal et al. |
| 2003/0100040 A1 | 5/2003 | Bonnecaze et al. | | 2004/0167383 A1 | 8/2004 | Kim et al. |
| 2003/0100821 A1 | 5/2003 | Heller et al. | | 2004/0167464 A1 | 8/2004 | Ireland et al. |
| 2003/0105407 A1 | 6/2003 | Pearce, Jr. et al. | | 2004/0167801 A1 | 8/2004 | Say et al. |
| 2003/0107487 A1 | 6/2003 | Korman et al. | | 2004/0171921 A1 | 9/2004 | Say et al. |
| 2003/0108976 A1 | 6/2003 | Braig et al. | | 2004/0176913 A1 | 9/2004 | Kawatahara et al. |
| 2003/0118460 A1 | 6/2003 | Lilie et al. | | 2004/0186362 A1 | 9/2004 | Brauker et al. |
| 2003/0130616 A1 | 7/2003 | Steil et al. | | 2004/0186365 A1 | 9/2004 | Jin et al. |
| 2003/0134347 A1 | 7/2003 | Heller et al. | | 2004/0193025 A1 | 9/2004 | Steil et al. |
| 2003/0135100 A1 | 7/2003 | Kim et al. | | 2004/0193090 A1 | 9/2004 | Lebel et al. |
| 2003/0135333 A1 | 7/2003 | Aceti et al. | | 2004/0199059 A1 | 10/2004 | Brauker et al. |
| 2003/0153820 A1 | 8/2003 | Berner et al. | | 2004/0202576 A1 | 10/2004 | Aceti et al. |
| 2003/0153821 A1 | 8/2003 | Berner et al. | | 2004/0207054 A1 | 10/2004 | Brown et al. |
| 2003/0154405 A1 | 8/2003 | Harrison | | 2004/0208780 A1 | 10/2004 | Faries, Jr. et al. |
| 2003/0158472 A1 | 8/2003 | Sohrab | | 2004/0210184 A1 | 10/2004 | Kost et al. |
| 2003/0158707 A1 | 8/2003 | Doi | | 2004/0225338 A1 | 11/2004 | Lebel et al. |
| 2003/0167035 A1 | 9/2003 | Flaherty et al. | | 2004/0236200 A1 | 11/2004 | Say et al. |
| 2003/0175806 A1 | 9/2003 | Rule et al. | | 2004/0248204 A1 | 12/2004 | Moerman |
| 2003/0176933 A1 | 9/2003 | Lebel et al. | | 2004/0249250 A1 | 12/2004 | McGee et al. |
| 2003/0181851 A1 | 9/2003 | Mann et al. | | 2004/0249253 A1 | 12/2004 | Racchini et al. |
| 2003/0181852 A1 | 9/2003 | Mann et al. | | 2004/0249254 A1 | 12/2004 | Racchini et al. |
| 2003/0187338 A1 | 10/2003 | Say et al. | | 2004/0249999 A1 | 12/2004 | Connolly et al. |
| 2003/0187525 A1 | 10/2003 | Mann et al. | | 2004/0253736 A1 | 12/2004 | Stout et al. |
| 2003/0191376 A1 | 10/2003 | Samuels et al. | | 2004/0254429 A1 | 12/2004 | Yang |
| 2003/0191431 A1 | 10/2003 | Mann et al. | | 2004/0254434 A1 | 12/2004 | Goodnow et al. |
| 2003/0195403 A1 | 10/2003 | Berner et al. | | 2004/0254884 A1 | 12/2004 | Haber et al. |
| 2003/0195462 A1 | 10/2003 | Mann et al. | | 2004/0263354 A1 | 12/2004 | Mann et al. |
| 2003/0198558 A1 | 10/2003 | Nason et al. | | 2004/0264396 A1 | 12/2004 | Ginzburg et al. |
| 2003/0199825 A1 | 10/2003 | Flaherty | | 2005/0003470 A1 | 1/2005 | Nelson et al. |
| 2003/0199837 A1 | 10/2003 | Vachon | | 2005/0009126 A1 | 1/2005 | Andrews et al. |
| 2003/0208110 A1 | 11/2003 | Mault et al. | | 2005/0010269 A1 | 1/2005 | Lebel et al. |
| 2003/0208113 A1* | 11/2003 | Mault et al. ................... 600/316 | | 2005/0016276 A1 | 1/2005 | Guan et al. |
| 2003/0208133 A1 | 11/2003 | Mault | | 2005/0027179 A1 | 2/2005 | Berner et al. |
| 2003/0208154 A1 | 11/2003 | Close et al. | | 2005/0027180 A1 | 2/2005 | Goode, Jr. et al. |
| 2003/0208409 A1 | 11/2003 | Mault | | 2005/0027181 A1 | 2/2005 | Goode, Jr. et al. |
| 2003/0212346 A1 | 11/2003 | Yuzhakov et al. | | 2005/0027462 A1 | 2/2005 | Goode, Jr. et al. |
| 2003/0212364 A1 | 11/2003 | Mann et al. | | 2005/0027463 A1 | 2/2005 | Goode, Jr. et al. |
| 2003/0212379 A1 | 11/2003 | Bylund et al. | | 2005/0031689 A1 | 2/2005 | Shults et al. |
| 2003/0217966 A1 | 11/2003 | Tapsak et al. | | 2005/0033132 A1 | 2/2005 | Shults et al. |
| 2003/0225360 A1 | 12/2003 | Eppstein et al. | | 2005/0038332 A1 | 2/2005 | Saidara et al. |
| 2003/0225361 A1 | 12/2003 | Sabra | | 2005/0038680 A1 | 2/2005 | McMahon |
| 2003/0226695 A1 | 12/2003 | Mault | | 2005/0043598 A1 | 2/2005 | Goode, Jr. et al. |
| 2003/0232370 A1 | 12/2003 | Trifiro | | 2005/0043894 A1 | 2/2005 | Fernandez |
| 2003/0235817 A1 | 12/2003 | Bartkowiak et al. | | 2005/0045476 A1 | 3/2005 | Neel et al. |
| 2004/0010207 A1 | 1/2004 | Flaherty et al. | | 2005/0049473 A1 | 3/2005 | Desai et al. |
| 2004/0011671 A1 | 1/2004 | Shults et al. | | 2005/0051580 A1 | 3/2005 | Ramey |
| 2004/0015131 A1 | 1/2004 | Flaherty et al. | | 2005/0053365 A1 | 3/2005 | Adams et al. |
| 2004/0018486 A1 | 1/2004 | Dunn et al. | | 2005/0054909 A1 | 3/2005 | Petisce et al. |
| 2004/0019321 A1 | 1/2004 | Sage et al. | | 2005/0059926 A1 | 3/2005 | Sage, Jr. et al. |
| 2004/0027253 A1 | 2/2004 | Marsh et al. | | 2005/0065464 A1 | 3/2005 | Talbot et al. |
| 2004/0030226 A1 | 2/2004 | Quy | | 2005/0090607 A1 | 4/2005 | Tapsak et al. |
| 2004/0039256 A1 | 2/2004 | Kawatahara et al. | | 2005/0090808 A1 | 4/2005 | Malave et al. |
| 2004/0041749 A1 | 3/2004 | Dixon | | 2005/0112169 A1 | 5/2005 | Brauker et al. |
| 2004/0045879 A1 | 3/2004 | Shults et al. | | 2005/0113653 A1 | 5/2005 | Fox et al. |
| 2004/0054263 A1 | 3/2004 | Moerman et al. | | 2005/0113657 A1 | 5/2005 | Alarcon et al. |
| 2004/0059201 A1 | 3/2004 | Ginsberg | | 2005/0113658 A1 | 5/2005 | Jacobson et al. |
| 2004/0059284 A1 | 3/2004 | Nash et al. | | 2005/0118726 A1 | 6/2005 | Scultz et al. |
| 2004/0064088 A1 | 4/2004 | Gorman et al. | | 2005/0121322 A1 | 6/2005 | Say et al. |
| 2004/0064096 A1 | 4/2004 | Flaherty et al. | | 2005/0124873 A1 | 6/2005 | Shults et al. |
| 2004/0064133 A1 | 4/2004 | Miller et al. | | 2005/0137471 A1 | 6/2005 | Haar et al. |

| | | | | | | |
|---|---|---|---|---|---|---|
| 2005/0143635 A1 | 6/2005 | Kamath et al. | | 2006/0063218 A1 | 3/2006 | Bartowiak et al. |
| 2005/0143636 A1 | 6/2005 | Zhang et al. | | 2006/0074564 A1 | 4/2006 | Bartkowiak et al. |
| 2005/0148003 A1 | 7/2005 | Keith et al. | | 2006/0094986 A1 | 5/2006 | Neel et al. |
| 2005/0154271 A1 | 7/2005 | Rasdal et al. | | 2006/0154642 A1 | 7/2006 | Scannell |
| 2005/0161346 A1 | 7/2005 | Simpson et al. | | 2006/0161078 A1 | 7/2006 | Schraga |
| 2005/0171503 A1 | 8/2005 | Van Den Berghe et al. | | 2006/0166629 A1 | 7/2006 | Reggiardo |
| 2005/0171512 A1 | 8/2005 | Flaherty | | 2006/0173259 A1 | 8/2006 | Flaherty et al. |
| 2005/0171513 A1 | 8/2005 | Mann et al. | | 2006/0173444 A1 | 8/2006 | Choy et al. |
| 2005/0173245 A1 | 8/2005 | Feldman et al. | | 2006/0173712 A1 | 8/2006 | Joubert |
| 2005/0176136 A1 | 8/2005 | Burd et al. | | 2006/0178633 A1 | 8/2006 | Garibotto et al. |
| 2005/0177036 A1 | 8/2005 | Shults et al. | | 2006/0222566 A1 | 10/2006 | Brauker et al. |
| 2005/0181012 A1 | 8/2005 | Saint et al. | | 2006/0224141 A1 | 10/2006 | Rush et al. |
| 2005/0182306 A1 | 8/2005 | Sloan | | 2006/0240403 A1 | 10/2006 | List et al. |
| 2005/0182358 A1 | 8/2005 | Veit et al. | | 2006/0247508 A1 | 11/2006 | Fennell |
| 2005/0182366 A1 | 8/2005 | Vogt et al. | | 2006/0253085 A1 | 11/2006 | Geismar et al. |
| 2005/0182451 A1 | 8/2005 | Griffin et al. | | 2006/0253086 A1 | 11/2006 | Moberg et al. |
| 2005/0187720 A1 | 8/2005 | Goode, Jr. et al. | | 2006/0273759 A1 | 12/2006 | Reggiardo |
| 2005/0192557 A1 | 9/2005 | Brauker et al. | | 2006/0282290 A1 | 12/2006 | Flaherty et al. |
| 2005/0195930 A1 | 9/2005 | Spital et al. | | 2006/0293577 A1 | 12/2006 | Morrison et al. |
| 2005/0199494 A1 | 9/2005 | Say et al. | | 2007/0016381 A1 | 1/2007 | Kamath et al. |
| 2005/0203360 A1 | 9/2005 | Brauker et al. | | 2007/0032717 A1 | 2/2007 | Brister et al. |
| 2005/0203461 A1 | 9/2005 | Flaherty et al. | | 2007/0078323 A1 | 4/2007 | Reggiardo et al. |
| 2005/0214892 A1 | 9/2005 | Kovatchev et al. | | 2007/0078818 A1 | 4/2007 | Zvitz et al. |
| 2005/0215871 A1 | 9/2005 | Feldman et al. | | 2007/0100222 A1 | 5/2007 | Mastrototaro et al. |
| 2005/0215872 A1 | 9/2005 | Berner et al. | | 2007/0106135 A1 | 5/2007 | Sloan |
| 2005/0218880 A1 | 10/2005 | Ioffe | | 2007/0118405 A1 | 5/2007 | Campbell et al. |
| 2005/0235732 A1 | 10/2005 | Rush | | 2007/0135697 A1 | 6/2007 | Reggiardo |
| 2005/0238503 A1 | 10/2005 | Rush et al. | | 2007/0163880 A1 | 7/2007 | Woo et al. |
| 2005/0238507 A1 | 10/2005 | DiIanni et al. | | 2007/0173711 A1 | 7/2007 | Shah et al. |
| 2005/0239154 A1 | 10/2005 | Feldman et al. | | 2007/0176867 A1 | 8/2007 | Reggiardo et al. |
| 2005/0239518 A1 | 10/2005 | D'Agostino et al. | | 2007/0203966 A1 | 8/2007 | Brauker et al. |
| 2005/0245795 A1 | 11/2005 | Goode, Jr. et al. | | 2007/0219480 A1 | 9/2007 | Kamen et al. |
| 2005/0245799 A1 | 11/2005 | Brauker et al. | | 2007/0219597 A1 | 9/2007 | Kamen et al. |
| 2005/0249506 A1 | 11/2005 | Fuse | | 2007/0235331 A1 | 10/2007 | Simpson et al. |
| 2005/0249606 A1 | 11/2005 | Rush | | 2008/0021666 A1 | 1/2008 | Goode, Jr. et al. |
| 2005/0251083 A1 | 11/2005 | Carr-Brendel et al. | | 2008/0033254 A1 | 2/2008 | Kamath et al. |
| 2005/0261660 A1 | 11/2005 | Choi | | 2008/0045824 A1 | 2/2008 | Tapsak et al. |
| 2005/0267550 A1 | 12/2005 | Hess et al. | | 2008/0064941 A1 | 3/2008 | Funderburk et al. |
| 2005/0267780 A1 | 12/2005 | Ray et al. | | 2008/0071156 A1 | 3/2008 | Brister et al. |
| 2005/0271546 A1 | 12/2005 | Gerber et al. | | 2008/0081977 A1 | 4/2008 | Hayter et al. |
| 2005/0271547 A1 | 12/2005 | Gerber et al. | | 2008/0083617 A1 | 4/2008 | Simpson et al. |
| 2005/0272640 A1 | 12/2005 | Doyle, III et al. | | 2008/0086042 A1 | 4/2008 | Brister et al. |
| 2005/0272985 A1 | 12/2005 | Kotulla et al. | | 2008/0086044 A1 | 4/2008 | Brister et al. |
| 2005/0277844 A1 | 12/2005 | Strother et al. | | 2008/0086273 A1 | 4/2008 | Shults et al. |
| 2005/0287620 A1 | 12/2005 | Heller et al. | | 2008/0097918 A1 | 4/2008 | Spector et al. |
| 2006/0001538 A1 | 1/2006 | Kraft et al. | | 2008/0103447 A1 | 5/2008 | Reggiardo et al. |
| 2006/0001550 A1 | 1/2006 | Mann et al. | | 2008/0108942 A1 | 5/2008 | Brister et al. |
| 2006/0001551 A1 | 1/2006 | Kraft et al. | | 2008/0119703 A1 | 5/2008 | Brister et al. |
| 2006/0003398 A1 | 1/2006 | Heller et al. | | 2008/0183061 A1 | 7/2008 | Goode et al. |
| 2006/0004271 A1 | 1/2006 | Peyser et al. | | 2008/0183399 A1 | 7/2008 | Goode et al. |
| 2006/0004603 A1 | 1/2006 | Peterka et al. | | 2008/0188731 A1 | 8/2008 | Brister et al. |
| 2006/0007017 A1 | 1/2006 | Mann et al. | | 2008/0189051 A1 | 8/2008 | Goode et al. |
| 2006/0015020 A1 | 1/2006 | Neale et al. | | 2008/0194935 A1 | 8/2008 | Brister et al. |
| 2006/0015024 A1 | 1/2006 | Brister et al. | | 2008/0194936 A1 | 8/2008 | Goode et al. |
| 2006/0016700 A1 | 1/2006 | Brister et al. | | 2008/0194937 A1 | 8/2008 | Goode et al. |
| 2006/0017923 A1 | 1/2006 | Ruchti et al. | | 2008/0194938 A1 | 8/2008 | Brister et al. |
| 2006/0019327 A1 | 1/2006 | Brister et al. | | 2008/0195049 A1 | 8/2008 | Thalmann et al. |
| 2006/0020186 A1 | 1/2006 | Brister et al. | | 2008/0195232 A1 | 8/2008 | Carr-Brendel et al. |
| 2006/0020187 A1 | 1/2006 | Brister et al. | | 2008/0195967 A1 | 8/2008 | Goode et al. |
| 2006/0020188 A1 | 1/2006 | Kamath et al. | | 2008/0197024 A1 | 8/2008 | Simpson et al. |
| 2006/0020189 A1 | 1/2006 | Brister et al. | | 2008/0200788 A1 | 8/2008 | Brister et al. |
| 2006/0020190 A1 | 1/2006 | Kamath et al. | | 2008/0200789 A1 | 8/2008 | Brister et al. |
| 2006/0020191 A1 | 1/2006 | Brister et al. | | 2008/0200791 A1 | 8/2008 | Simpson et al. |
| 2006/0020192 A1 | 1/2006 | Brister et al. | | 2008/0200838 A1 | 8/2008 | Goldberger et al. |
| 2006/0025663 A1 | 2/2006 | Talbot et al. | | 2008/0200897 A1 | 8/2008 | Hoss et al. |
| 2006/0031094 A1 | 2/2006 | Cohen et al. | | 2008/0208025 A1 | 8/2008 | Shults et al. |
| 2006/0036139 A1 | 2/2006 | Brister et al. | | 2008/0214915 A1 | 9/2008 | Brister et al. |
| 2006/0036140 A1 | 2/2006 | Brister et al. | | 2008/0214918 A1 | 9/2008 | Brister et al. |
| 2006/0036141 A1 | 2/2006 | Kamath et al. | | 2008/0228051 A1 | 9/2008 | Shults et al. |
| 2006/0036142 A1 | 2/2006 | Brister et al. | | 2008/0228054 A1 | 9/2008 | Shults et al. |
| 2006/0036143 A1 | 2/2006 | Brister et al. | | 2008/0228055 A1 | 9/2008 | Sher |
| 2006/0036144 A1 | 2/2006 | Brister et al. | | 2008/0242961 A1 | 10/2008 | Brister et al. |
| 2006/0036145 A1 | 2/2006 | Brister et al. | | 2008/0262469 A1 | 10/2008 | Brister et al. |
| 2006/0036187 A1 | 2/2006 | Vos et al. | | 2008/0275313 A1 | 11/2008 | Brister et al. |
| 2006/0040402 A1 | 2/2006 | Brauker et al. | | 2008/0287764 A1 | 11/2008 | Rasdal et al. |
| 2006/0041229 A1 | 2/2006 | Garibotto et al. | | 2008/0287765 A1 | 11/2008 | Rasdal et al. |
| 2006/0052679 A1 | 3/2006 | Kotulla et al. | | 2008/0287766 A1 | 11/2008 | Rasdal et al. |
| 2006/0058602 A1 | 3/2006 | Kwiatkowski et al. | | 2008/0296155 A1 | 12/2008 | Shults et al. |
| 2006/0058627 A1 | 3/2006 | Flaherty et al. | | 2008/0306368 A1 | 12/2008 | Goode et al. |

| | | |
|---|---|---|
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312844 A1 | 12/2008 | Hayter et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0063196 A1 | 3/2009 | Frederickson |
| 2009/0063402 A1* | 3/2009 | Hayter .............................. 707/2 |
| 2009/0068954 A1 | 3/2009 | Reggiardo et al. |
| 2009/0069750 A1 | 3/2009 | Schraga |
| 2009/0076356 A1 | 3/2009 | Simpson et al. |
| 2009/0076358 A1 | 3/2009 | Reggiardo et al. |
| 2009/0076360 A1 | 3/2009 | Brister et al. |
| 2009/0076361 A1 | 3/2009 | Kamath et al. |
| 2009/0083003 A1 | 3/2009 | Reggiardo et al. |
| 2009/0099436 A1 | 4/2009 | Brister et al. |
| 2009/0105636 A1 | 4/2009 | Hayter et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0216553 A1 | 8/2009 | Cellura |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0259118 A1 | 10/2009 | Feldman et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |
| 2010/0241447 A1 | 9/2010 | Siniaguine et al. |

FOREIGN PATENT DOCUMENTS

| | | |
|---|---|---|
| EP | 0518524 | 12/1992 |
| EP | 0709573 | 5/1996 |
| EP | 0878707 | 11/1998 |
| EP | 0543916 | 7/2001 |
| EP | 1130638 | 9/2001 |
| EP | 0980688 | 12/2002 |
| EP | 1755443 | 11/2005 |
| EP | 1783536 | 5/2007 |
| FR | 2718492 | 10/1995 |
| JP | 1-080775 | 3/1989 |
| JP | 2001-177423 | 6/2001 |
| JP | 2001-056673 | 11/2001 |
| WO | WO-96/14026 | 5/1996 |
| WO | WO-96/34637 | 11/1996 |
| WO | WO-99/22236 | 5/1999 |
| WO | WO-99/56613 | 11/1999 |
| WO | WO-00/74753 | 12/2000 |
| WO | WO-01/41849 | 6/2001 |
| WO | WO-01/52727 | 7/2001 |
| WO | WO-01/54753 | 8/2001 |
| WO | WO-01/71186 | 9/2001 |
| WO | WO-02/39086 | 5/2002 |
| WO | WO-02/057627 | 7/2002 |
| WO | WO-02/058537 | 8/2002 |
| WO | WO-02/084860 | 10/2002 |
| WO | WO-02/100263 | 12/2002 |
| WO | WO-02/100469 | 12/2002 |
| WO | WO-03/006091 | 1/2003 |
| WO | WO-03/090509 | 4/2003 |
| WO | WO-03/053503 | 7/2003 |
| WO | WO-03/071930 | 9/2003 |
| WO | WO-03/103763 | 12/2003 |
| WO | WO-2004/028337 | 4/2004 |
| WO | WO-2004/032994 | 4/2004 |
| WO | WO-2004/061420 | 7/2004 |
| WO | WO-2005/089103 | 9/2005 |
| WO | WO-2005/101994 | 11/2005 |
| WO | WO-2006/003919 | 1/2006 |
| WO | WO-2006/079114 | 7/2006 |
| WO | WO-2006/086701 | 8/2006 |
| WO | WO-2006/102412 | 9/2006 |
| WO | WO-2006/110913 | 10/2006 |
| WO | WO-2006/113408 | 10/2006 |
| WO | WO-2006/113521 | 10/2006 |
| WO | WO-2006/118947 | 11/2006 |
| WO | WO-2006/132884 | 12/2006 |
| WO | WO-2007/041072 | 4/2007 |
| WO | WO-2007/090037 | 8/2007 |
| WO | WO-2008/055037 | 5/2008 |
| WO | WO-2008/086541 | 7/2008 |
| WO | WO-2008/110267 | 9/2008 |

OTHER PUBLICATIONS

"An Electrochemical Slow Flow Meter", http://gore.ocean.washington.edu/research/slow_flow_meter.html, 2005, 3 pages.

Barbosa, R. M., et al., "Electrochemical Studies of Zinc in Zinc-

Insulin Solution", *Journal of the Royal Society of Chemistry, Analyst*, vol. 121, No. 12, 1996, pp. 1789-1793.

Bard, A. J., et al., "Methods Involving Forced Convection—Hydrodynamic Methods", *Electrochemical Methods—Fundamentals and Applications*, 2001, pp. 331-367.

Kissinger, P. T., "Introduction to Analog Instrumentation", *Laboratory Techniques in Electroanalytical Chemistry, Second Edition, Revised and Expanded*, 1996, pp. 165-194.

Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.

PCT Application No. PCT/US2010/032861, International Search Report and Written Opinion of the International Searching Authority mailed Jun. 28, 2010.

\* cited by examiner

CLOSED LOOP BLOOD GLUCOSE CONTROL ALGORITHM ANALYSIS

RELATED APPLICATIONS

The present application claims priority under 35 U.S.C. §119(e) to U.S. provisional application No. 61/173,598 filed Apr. 28, 2009, entitled "Closed Loop Blood Glucose Control Algorithm Analysis", the disclosure of which is incorporated in its entirety by reference for all purposes.

BACKGROUND

A desirable diabetes management and treatment includes a combined continuous blood glucose monitoring and insulin delivery system that operate autonomously. In such systems, control software would monitor the output of the continuous blood glucose monitor and calculate appropriate delivery instructions for the insulin delivery system. Such a system is often referred to as closed loop blood glucose control and the control software is often referred to as a closed loop blood glucose control algorithm.

The development of a closed loop blood glucose control algorithm is the most challenging aspect of the development of a closed loop blood glucose control system. This challenge arises from complicated features of diabetes management such as noise and delays that are inherent features of blood glucose monitoring and insulin delivery. Another complicating aspect of developing a closed loop blood glucose control algorithm is that individuals can differ significantly in the details of their lifestyle (e.g., diet, activity level) and in the details of their physiology (e.g., size, fitness, insulin sensitivity).

Furthermore, failure of a closed loop blood glucose control algorithm could potentially have lethal consequences. Thus a closed loop blood glucose control algorithm will need to be comprehensively tested and likely need to be tuned or personalized to each individual user.

Currently, testing a closed loop blood glucose control algorithm requires the use of a living diabetic subject or a mathematical model of a diabetic subject. The living subject can be animal or human. Testing a closed loop blood glucose control algorithm on a living subject suffers from the disadvantage that such testing is expensive, time consuming and poses significant risks to the health of the test subject. Testing a closed loop blood glucose control algorithm with a mathematical model of a diabetic subject suffers from the fact that human physiology is far too complex to be sufficiently represented by any currently available mathematical model. The main advantage of the method described herein is that it is fast, inexpensive and incurs no risk and also captures the inherent complexity of a live diabetic subject.

SUMMARY

Embodiments of the subject disclosure include device and methods comprising receiving glucose data for a predetermined time period, determining a variation in the glucose level based on the received glucose data, filtering a received glucose data based on the determined variation, substituting a negative change in the glucose data value with a predetermined value to generate a sequence of modified glucose values, and integrating the sequence of modified glucose values to determine an uncontrolled blood glucose excursion condition.

An apparatus in a further aspect includes a user interface, one or more processors operatively coupled to the data user interface, and a memory for storing instructions which, when executed by the one or more processors, causes the one or more processors to receive glucose data for a predetermined time period, determine a variation in the glucose level based on the received glucose data, filter a received glucose data based on the determined variation, substitute a negative change in the glucose data value with a predetermined value to generate a sequence of modified glucose values, and integrating the sequence of modified glucose values to determine an uncontrolled blood glucose excursion condition.

In still another aspect, one or more storage devices having processor readable code embodied thereon, the processor readable code for programming one or more processors to perform a control test algorithm comprising receiving glucose data for a predetermined time period, determining a variation in the glucose level based on the received glucose data, filtering a received glucose data based on the determined variation, substituting a negative change in the glucose data value with a predetermined value to generate a sequence of modified glucose values, and integrating the sequence of modified glucose values to determine an uncontrolled blood glucose excursion condition.

Also provided are systems, computer program products, and kits.

INCORPORATION BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,167,818; and 7,299,082; U.S. Published Application Nos. 2004/0186365; 2005/0182306; 2007/0056858; 2007/0068807; 2007/0227911; 2007/0233013; 2008/0081977; 2008/0161666; and 2009/0054748; U.S. patent application Ser. Nos. 11/831,866; 11/831,881; 11/831,895; 12/102,839; 12/102,844; 12/102,847; 12/102,855; 12/102,856; 12/152,636; 12/152,648; 12/152,650; 12/152,652; 12/152,657; 12/152,662; 12/152,670; 12/152,673; 12/363,712; 12/131,012; 12/242,823; 12/363,712; 12/393,921; 12/495,709; 12/698,124; 12/699,653; 12/699,844; 12/714,439; 12/761,372; and 12/761,387 and U.S. Provisional Application Ser. Nos. 61/230,686 and 61/227,967.

DETAILED DESCRIPTION

Figure 1:
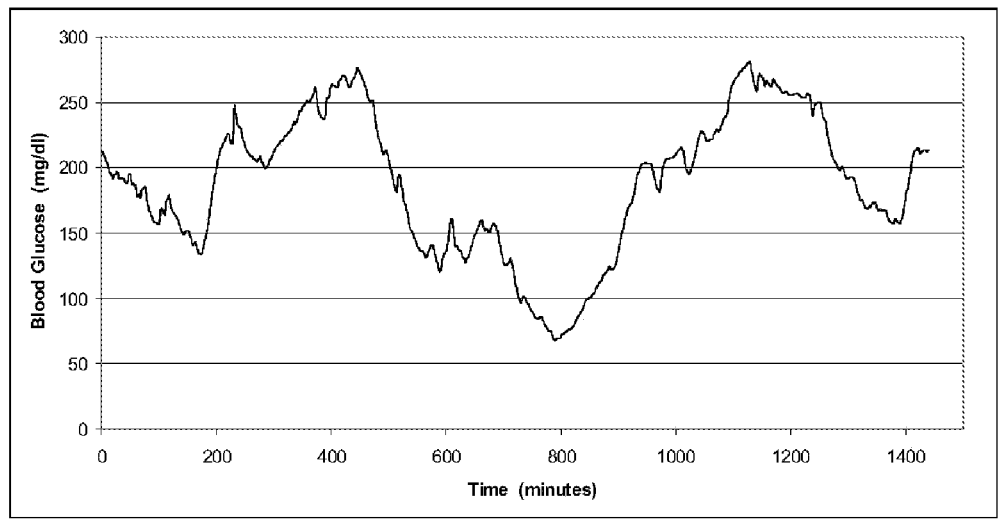
FIG. 1 is a graphical illustration of blood glucose data using a continuous glucose monitoring system in accordance with aspects of the present disclosure.

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. That the upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure are directed to developing and testing a closed loop blood glucose control algorithm. The embodiments disclosed herein use continuous blood glucose data to construct a realistic test input that may be used as an aid in developing, testing or tuning a closed loop blood glucose control algorithm. In one aspect, the algorithm analyzes a set of continuous blood glucose data and processes it to generate a hypothetical uncontrolled blood glucose excursion. This uncontrolled blood glucose excursion can then be used as a test input to aid in developing, testing or tuning a closed loop blood glucose control algorithm. In one aspect, the approach described in accordance with the various embodiments allows a closed loop blood glucose control algorithm to be custom tailored to the unique requirements of a diabetic individual.

In one aspect, analysis may be performed on continuously monitored glucose data to generate a tool that may be used to develop, test or tune a closed loop blood glucose control algorithm. A set of continuous blood glucose data shows the increases and decreases in blood glucose corresponding to various metabolic processes that add glucose to or remove glucose from the body. For a diabetic person with poor blood glucose control, these increases and decreases in blood glucose can be very distinct because consumption of carbohydrates and injection of insulin are not well matched.

FIG. 1 shows a plot of glucose data generated using a continuous glucose monitoring system such as, for example, Freestyle Navigator® Continuous Glucose Monitoring System available from Abbott Diabetes Care Inc., Alameda Calif. It can be seen that the continuous glucose data shown FIG. 1 includes data from a diabetic subject with poor glucose control over a 24 hour period with data points obtained every one minute. As can be further seen from FIG. 1, the overall data set is composed of distinct subsets of data in which blood glucose is continuously increasing (upslopes shown in FIG. 1) and distinct subsets of data in which blood glucose is continuously decreasing (downslopes shown in FIG. 1).

Additional detailed descriptions of embodiments of the analyte monitoring system, embodiments of its various components are provided in U.S. Pat. Nos. 5,262,035; 5,264,104; 5,262,305; 5,320,715; 5,593,852; 6,103,033; 6,134,461; 6,175,752; 6,560,471; 6,579,690; 6,605,200; 6,654,625; 6,746,582; and 6,932,894; and in U.S. Published Patent Application No. 2004/0186365, the disclosures of which are herein incorporated by reference. Furthermore, detailed description of signal processing related to sensor initialization, signal filtering, and processing in analyte monitoring systems can be found in U.S. Pat. Nos. 6,175,751, 6,560,471, and in U.S. patent application Ser. No. 12/152,649 filed May 14, 2008, disclosure of each of which are incorporated herein by reference for all purposes. Additionally, details of closed loop control system with safety parameters are described in U.S. Published Patent Application No. US2009/0105636 filed Aug. 31, 2008, the disclosure of which is incorporated herein by reference for all purposes.

As discussed above, this pattern or distinct subset may be an indication that for the individual from whom the data set was derived, consumption of carbohydrates and injection of insulin are not well matched. Accordingly, in one aspect of the present disclosure, the subsets of data in which blood glucose is continuously increasing may be separated from the subsets of data in which blood glucose is continuously decreasing. The subsets of data in which blood glucose is decreasing are then removed and replaced with an artificially constructed subset of blood glucose data that serves as an extrapolation of the subset of increasing blood glucose data that preceded it. In one aspect, the subsets of data in which blood glucose is continuously increasing and the artificially constructed subset of blood glucose data may be associated or linked together. This results in a plot of how blood glucose level increases with time if glucose was never consumed i.e., a hypothetical uncontrolled blood glucose excursion. This hypothetical uncontrolled blood glucose excursion may then be used as a test input to a closed loop blood glucose control algorithm to aid in developing, testing or tuning that algorithm. This analysis of the blood glucose data can readily be performed using a conventional software program such as a spreadsheet program.

In one aspect of the present disclosure, continuously monitored glucose data such as that shown in FIG. 1 is collected. As the collected data indicates, for example, shown in FIG. 1, the increase and decrease of blood glucose value over time may be due to various metabolic processes including the influx of glucose from the gut, release and uptake of glucose from the liver and insulin dependent utilization of glucose by cells in the body. The collected data may be uploaded into a spreadsheet program for processing as a time sequential data. For reference, the time stamp for each data point is associated with each one minute data. The resulting data is then plotted as, for example, shown in FIG. 1.

Figure 2:
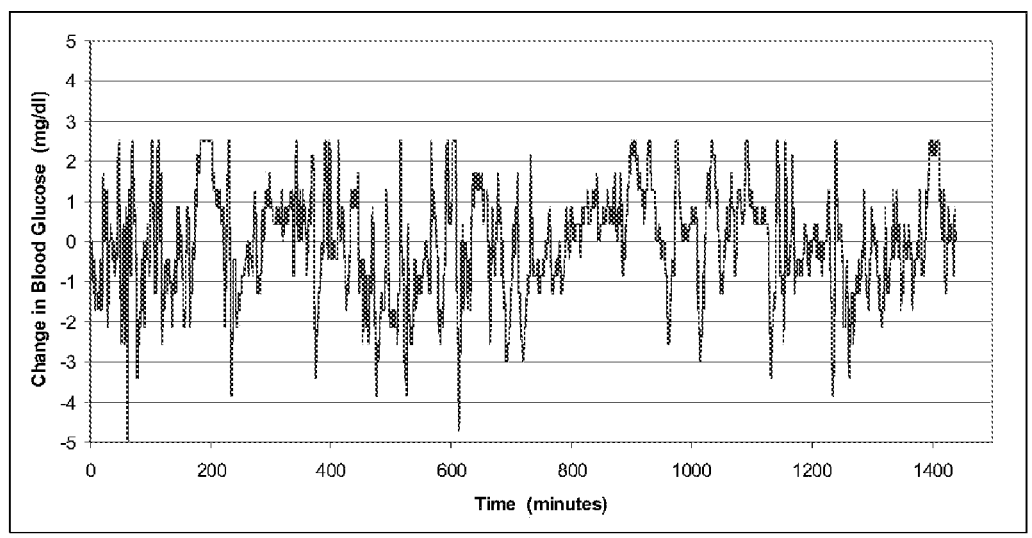
FIG. 2 is a graphical illustration of filtered minute to minute changes in blood glucose data from the data set shown in FIG. 1 in aspects of the present disclosure.

Using the collected and/or plotted data set, the change in glucose value from one minute to the next is determined. For example, the change in blood glucose value from one minute to the next can be determined. In one aspect, minute to minute variation in blood glucose level that are unrealistically large may also be filtered out as they are likely due to noise or signal artifacts in the continuous glucose sensor. For example, it can be seen that a rate of change in blood glucose level greater than 2.5 mg/dl per minute is likely to be caused by noise in the continuous blood glucose monitoring system. FIG. 2 illustrates a plot of the filtered minute to minute changes in blood glucose data based on the data of FIG. 1.

As a separate set of data, in one aspect, negatively valued changes in blood glucose are filtered out and replaced. In one aspect, different approaches or values may be used for replacement values to separate the subsets of blood glucose data where blood glucose is increasing from those subsets of data where blood glucose is decreasing. The subsets of blood glucose data where blood glucose is increasing are then linked or associated with an artificially constructed subset of blood glucose data. The artificially constructed subset of blood glucose data is generated so as to effect an extrapolation of the previous subset of blood glucose data where blood glucose is increasing.

Specifically, in one embodiment, negatively valued changes in blood glucose may be replaced with a zero value. In this manner, the artificially constructed subset of blood glucose data has the effect of holding the blood glucose constant between the subsets of increasing blood glucose. An example of how this would be implemented as a logic statement is shown in equation 1 below where "n" is the specific blood glucose value in question.

$$\text{if } n<0, \text{ then } n=0, \text{ otherwise } n=n \quad (1)$$

In an alternative embodiment negatively valued changes in blood glucose are replaced with a constant positive value. In this manner, the artificially constructed subset of blood glucose data may be generated so as to affect a constant increase in blood glucose value. An example of how this would be implemented as a logic statement is shown in equation 2 below where "n" is to the specific blood glucose value in question and "x" is the constant rate of blood glucose increase in the artificially constructed subset of blood glucose data.

$$\text{if } n<0, \text{ then } n=x, \text{ otherwise } n=n \quad (2)$$

In yet a further embodiment, negatively valued changes in blood glucose may be replaced with an average value of all or part of the previous subset of increasing blood glucose value. In this manner, the glucose trend that was present in the previous subset of increasing blood glucose value may be preserved in the artificially constructed subset of blood glucose data. The artificially constructed subset of blood glucose data may extrapolate the trend in blood glucose data that was present in the previous subset of blood glucose data that was increasing. An example of this approach as a logic statement is shown in equation 3 below where "n" is the specific blood glucose value in question and "y" is the number of previous positively valued blood glucose values which are averaged.

$$\text{if } n<0, \text{ then } n=\text{average previous y positive values,} \text{ otherwise } n=n \quad (3)$$

Figure 3:
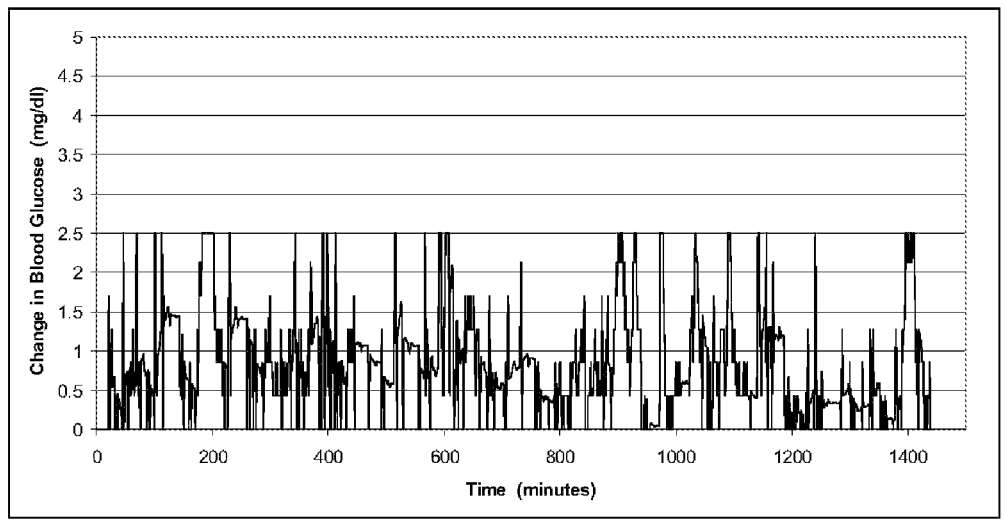
FIG. 3 is a graphical illustration of filtered minute to minute changes in blood glucose data from the data set shown in FIG. 1 in aspects of the present disclosure.

FIG. 3 illustrates a plot of the aforementioned filtered minute to minute changes in blood glucose data. As can be seen, the subsets of data where blood glucose level is decreasing are removed by replacing negatively valued changes in blood glucose with the average of the previous 10 positively valued changes in blood glucose.

In still a further embodiment, the negatively valued changes in blood glucose may be replaced with a blood glucose value that is a predefined function of all or part of the previous subset of increasing blood glucose values. For example, a linear regression curve fit may be applied to all or part of the previous subset of increasing blood glucose values. This linear regression curve fit may be used to extrapolate values to replace decreasing blood glucose values. Alternatively, a higher order curve fit may be applied to all or part of the previous subset of increasing blood glucose values. This curve fit can then be used to extrapolate values to replace decreasing blood glucose values.

After obtaining the filtered analyzed data set as discussed above, the minute to minute positive changes in blood glucose level are integrated into a continuous uncontrolled blood glucose excursion. In one aspect, integrating the minute to minute positive changes in blood glucose level into the continuous uncontrolled blood glucose excursion may be achieved by selecting a blood glucose value to start with, for example, 100 mg/dl, and adding each minute's blood glucose change to this initial value.

Figure 4:
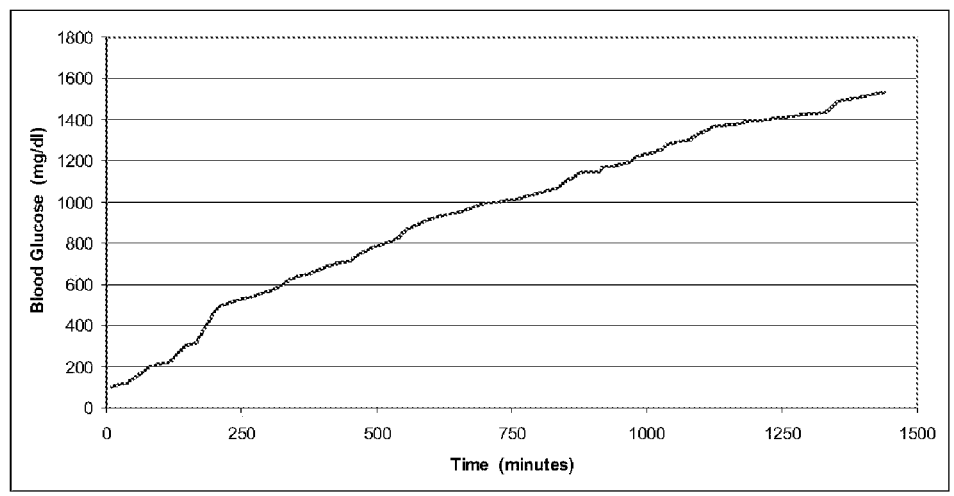
FIG. 4 is a graphical illustration of an uncontrolled blood glucose excursion generated from the data in FIG. 3 in aspects of the present disclosure.

FIG. 4 illustrates a plot of an uncontrolled blood glucose excursion generated from the data in FIG. 3. The plot shown in FIG. 4 includes all of the actual subsets of blood glucose data from FIG. 1 where blood glucose is increasing linked together with artificially constructed subsets of blood glucose data that are extrapolations of the subsets of increasing blood glucose data that preceded them. The uncontrolled blood glucose excursion in FIG. 4 shows a change in blood glucose of about 1400 mg/dl over the course of 24 hrs. For a 70 kg person, this may result from the consumption of about 200 grams (1000 calories) of carbohydrates which is a reasonable amount for a daily consumption. Moreover, as shown in FIG. 4, the subtle features and irregularities of blood glucose data that arise as a result of the unique features of an individual's lifestyle and physiology are illustrated.

Figure 5:
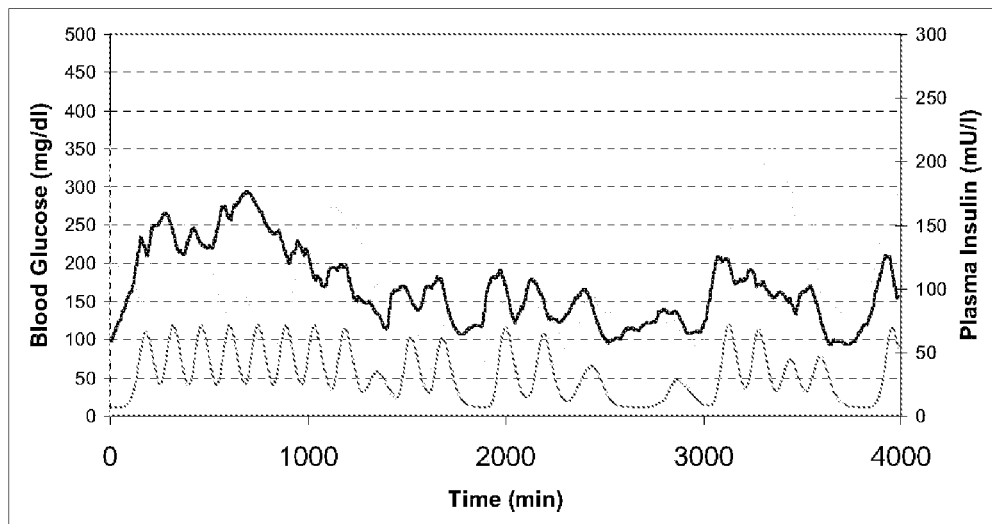
FIG. 5 is a graphical illustration of an example of output from a closed loop control simulation in accordance with embodiments of the present disclosure.

In one aspect, the profile illustrated in FIG. 4 is used as a test input to a closed loop control simulation. FIG. 5 illustrates an example of output from a simple closed loop control simulation. The simulation uses the data in FIG. 4 as a test input and a PID control algorithm. The control simulation additionally uses a model for insulin sensitivity and for insulin pharmacokinetics. Blood glucose is shown on the upper curve and insulin concentration is shown on the lower curve.

The insulin concentration is due to insulin that was administered by the controller in response to the blood glucose behavior in FIG. 4. The various values for controller gain can readily be changed to affect optimal control. Values for insulin sensitivity and insulin pharmacokinetics as well as parameters for the continuous blood glucose monitor's performance can also be changed to assess the robustness of the controller.

Figure 6:
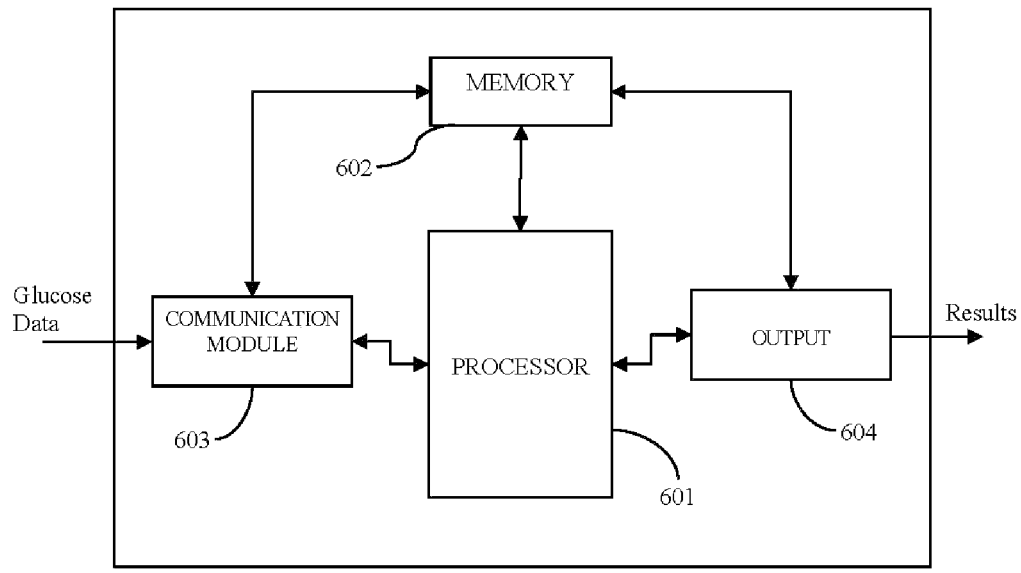
FIG. 6 is a block diagram illustrating an overall system for executing closed loop control simulation routines in accordance with embodiments of the present disclosure.

FIG. 6 is a block diagram illustrating an overall system for executing closed loop control simulation routines in accordance with embodiments of the present disclosure. Referring to FIG. 6, in certain embodiments, data, such as glucose data, for use in the closed loop control simulation routines described above, is received at a system 600 via a communication module 603. The communication module 603 may be a wired connection port configured to receive data via a wired connection, such as, among others, a universal serial bus (USB) connection, RS-232 serial connection, parallel connection, or Ethernet connection, or may be a wireless communication module configured for, among others, radio frequency (RF) communication protocol, Bluetooth® communication protocol, infrared (IR) communication protocol, or 802.11 WiFi communication protocol. The communication module 603 is coupled to a processor 601 or other processing unit. The processor 601, may be, among others, a microprocessor, microcontroller, CPU, or an application specific integrated circuit (ASIC). The processor 601 and the communication module 603 are also coupled to a memory 602. In certain embodiments, the memory 602 may be integral with the processor 601. In other embodiments, the memory 602 may be a separate unit external from the processor 601 unit and coupled via a communication interface.

Still referring to FIG. 6, the glucose data received at the communication module 603 is stored in the memory 602 under control of the processor 601. The memory 602 additionally stores programming instructions for execution by the processor 601 for executing closed loop control simulation routines, such as the closed loop control simulation routines described above, based on the glucose data received at the communication module 603 and stored in the memory 602. The system may further include an output module 604 configured for transmission or output of the results of the closed loop control simulation routines. In certain embodiments the output module 604 transmits the results of the closed loop control simulation routines to an external display device for display to a patient or user. In other embodiments the output module 604 of the system 600 is a display or other output device for displaying or otherwise outputting (for example via audio output) results of the closed loop control simulation routines to the user.

In this manner, in aspects of the present disclosure it can be seen that for a diabetic person with poor blood glucose control, a set of continuous blood glucose data collected over a long period of time may include significant subsets of continuous data where the measured change in blood glucose is dominated by the influx of glucose from the gut and where insulin dependent utilization of glucose contributes insignificantly. In these subsets of continuous data, blood glucose level rises at or near its maximum possible rate. Accordingly, in one aspect, the one or more routines described herein links or associates those subsets of continuous data together with artificially constructed subsets of blood glucose data that are extrapolations of the blood glucose data that preceded them. This forms a hypothetical uncontrolled blood glucose excursion which can then be used as a tool in the development, testing and tuning of a closed loop blood glucose control algorithm.

A method for developing and testing a closed loop blood glucose control algorithms is disclosed. The method uses continuous blood glucose data to develop, test or tune a closed loop blood glucose control algorithm. The process takes a string of continuous blood glucose data and mathematically processes it to produce a hypothetical uncontrolled blood glucose excursion. This uncontrolled blood glucose excursion can then be used as a test input to aid in developing, testing or tuning a closed loop blood glucose control algorithm. This method will allow a closed loop blood glucose control algorithm to be custom tailored to the unique requirements of an individual.

In the manner described above, in accordance with embodiments of the present disclosure, method for developing and testing a closed loop blood glucose control algorithm is provided. In one aspect, continuous blood glucose data may be used to generate a test input that can be used as an aid in developing, testing or tuning a closed loop blood glucose control algorithm. The routine may include a set of continuous blood glucose data which is analyzed to generate or determine a hypothetical uncontrolled blood glucose excursion. The uncontrolled blood glucose excursion may be used as a test input to aid in developing, testing or tuning a closed loop blood glucose control algorithm. In one aspect, this approach may allow a closed loop blood glucose control algorithm to be custom tailored to the unique requirements of a diabetic individual.

In one embodiment, a method may include receiving glucose data for a predetermined time period, determining a variation in the glucose level based on the received glucose data, filtering the received glucose data based on the determined variation, substituting a negative change in the glucose data value with a predetermined value to generate a sequence of modified glucose values, and integrating the sequence of modified glucose values to determine an uncontrolled blood glucose excursion condition.

In one aspect, the predetermined value may include an average value, where the average value may include an average of ten prior values. Alternatively, or in addition to, the average value may include a weighted average value, which may be an equally or unequally weighted average value.

In a further aspect, filtering based on the predetermined variation may include filtering out glucose values associated with a negative change, where the negative change may be determined based on an immediate prior glucose value.

In another embodiment, an apparatus is disclosed which may include a user interface, one or more processors operatively coupled to the user interface, and a memory for storing instructions which, when executed by the one or more processors, causes the one or more processors to receive glucose data for a predetermined time period, determine a variation in the glucose level based on the received glucose data, filter the received glucose data based on the determined variation, substitute a negative change in the glucose data value with a predetermined value to generate a sequence of modified glucose values, and integrating the sequence of modified glucose values to determine an uncontrolled blood glucose excursion condition.

In another aspect, the memory for storing instructions which, when executed by the one or more processors, may cause the one or more processors to filter out glucose values associated with a negative change, where the negative change may be determined based on an immediate prior glucose value.

In still another aspect, one or more storage devices having processor readable code embodied thereon, said processor readable code for programming one or more processors to perform a control test algorithm may comprise receiving glucose data for a predetermined time period, determining a variation in the glucose level based on the received glucose data, filtering the received glucose data based on the determined variation, substituting a negative change in the glucose data value with a predetermined value to generate a sequence of modified glucose values, and integrating the sequence of modified glucose values to determine an uncontrolled blood glucose excursion condition.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A method, comprising:
receiving, at one or more processors, analyte data for a predetermined time period;
comparing, using the one or more processors, at least two consecutive analyte data values in the received analyte data;
determining, using the one or more processors, a variation in an analyte level based on the comparison;
filtering, using the one or more processors, the received analyte data based on the determined variation;
substituting, using the one or more processors, one or more analyte data values associated with a decrease in analyte concentration with a predetermined value;
generating, using the one or more processors, a sequence of modified analyte values based upon the substitution;
integrating, using the one or more processors, the sequence of modified analyte values; and
determining, using the one or more processors, an uncontrolled analyte excursion condition based upon the integration.

2. The method of claim 1 wherein the predetermined value includes an average value.

3. The method of claim 2 wherein the average value includes an average of ten prior values.

4. The method of claim 2 wherein the average value includes a weighted average value.

5. The method of claim 4 wherein the weighted average value includes an equally weighted average value.

6. The method of claim 4 wherein the weighted average value includes an unequally weighted average value.

7. The method of claim 2 wherein the average value includes an unweighted average value.

8. The method of claim 1 wherein filtering based on the determined variation includes filtering out the one or more analyte values associated with the decrease in analyte concentration.

9. The method of claim 8 wherein the decrease in analyte concentration is determined based on the comparison of the at least two consecutive analyte data values in the received analyte data.

10. An apparatus, comprising:
a user interface;
one or more processors operatively coupled to the user interface; and
a memory for storing instructions which, when executed by the one or more processors, causes the one or more processors to receive analyte data for a predetermined time period, to compare at least two consecutive analyte data values in the received analyte data, to determine a variation in the analyte level based on the comparison, to filter the received analyte data based on the determined variation, to substitute one or more analyte data values associated with a decrease in analyte concentration with a predetermined value, to generate a sequence of modified analyte values based upon the substitution, to integrate the sequence of modified analyte values, and to determine an uncontrolled analyte excursion condition based upon the integration.

11. The apparatus of claim 10 wherein the predetermined value includes an average value.

12. The apparatus of claim 11 wherein the average value includes an average of ten prior values.

13. The apparatus of claim 10 wherein the average value includes a weighted average value.

14. The apparatus of claim 13 wherein the weighted average value includes an equally weighted average value.

15. The apparatus of claim 13 wherein the weighted average value includes an unequally weighted average value.

16. The apparatus of claim 10 wherein the average value includes an unweighted average value.

17. The apparatus of claim 10 wherein the memory for storing instructions which, when executed by the one or more processors, causes the one or more processors to filter out the one or more analyte values associated with the decrease in analyte concentration.

18. The apparatus of claim 17 wherein the decrease in analyte concentration is determined based on the comparison of the at least two consecutive analyte data values in the received analyte data.

19. The method of claim 1 further comprising performing a test input of a closed loop control simulation using the determined uncontrolled analyte excursion condition.

20. The apparatus of claim 10 wherein the memory for storing instructions which, when executed by the one or more processors, causes the one or more processors to perform a test input of a closed loop control simulation using the determined uncontrolled analyte excursion condition.

* * * * *